(12) United States Patent
Krespi et al.

(10) Patent No.: US 12,318,138 B2
(45) Date of Patent: Jun. 3, 2025

(54) DEVICE AND METHODS OF LASER TREATMENT FOR RHINOLOGY

(71) Applicant: Valam Corporation, Ridgefield, CT (US)

(72) Inventors: Yosef Krespi, Ridgefield, CT (US); Ron Hadani, Even-Yehuda (IL)

( * ) Notice: Subject to any disclaimer, the term of this patent is extended or adjusted under 35 U.S.C. 154(b) by 366 days.

(21) Appl. No.: 17/841,565

(22) Filed: Jun. 15, 2022

(65) Prior Publication Data

US 2022/0395327 A1 Dec. 15, 2022

Related U.S. Application Data

(60) Provisional application No. 63/210,992, filed on Jun. 15, 2021.

(51) Int. Cl.
| | | |
|---|---|---|
| A61B 18/20 | (2006.01) | |
| A61B 18/22 | (2006.01) | |
| A61B 17/00 | (2006.01) | |
| A61B 18/00 | (2006.01) | |

(52) U.S. Cl.
CPC ...... *A61B 18/22* (2013.01); *A61B 2017/0023* (2013.01); *A61B 2018/00327* (2013.01); *A61B 2018/00577* (2013.01); *A61B 2018/2253* (2017.05)

(58) Field of Classification Search
CPC ............ A61B 18/20; A61N 5/06; A61F 9/008
See application file for complete search history.

(56) References Cited

U.S. PATENT DOCUMENTS

| | | |
|---|---|---|
| 6,355,032 B1 | 3/2002 | Hovda et al. |
| 6,416,491 B1 | 7/2002 | Edwards et al. |
| 7,442,191 B2 | 10/2008 | Hovda et al. |
| 8,425,457 B2 | 4/2013 | John et al. |
| 8,747,401 B2 | 6/2014 | Gonzalez et al. |
| 9,649,144 B2 | 5/2017 | Aluru et al. |
| 9,833,276 B2 | 12/2017 | Newman |
| 9,943,361 B2 | 4/2018 | Wolf et al. |
| 10,456,185 B2 | 10/2019 | Wolf et al. |
| 10,470,837 B2 | 11/2019 | Lin et al. |
| 10,492,810 B2 | 12/2019 | Chang et al. |
| 10,575,893 B2 | 3/2020 | Mayse |

(Continued)

FOREIGN PATENT DOCUMENTS

| | | |
|---|---|---|
| AU | 2012202103 A1 | 5/2012 |
| EP | 1039862 B1 | 5/2008 |

(Continued)

*Primary Examiner* — Lynsey C Eiseman
(74) *Attorney, Agent, or Firm* — Joseph P. Aiena

(57) ABSTRACT

There is provided a process for treatment of rhinitis by diode laser ablation of the branches of the posterior nasal nerve. The diode laser delivery device with elongated fiber optic with its fiber tip is inserted through a patient's nostril and has the length, flexibility and a curvature to reach both above and under the patient's middle turbinate for treatment of both branches of the posterior nasal nerves. Skin and tissue temperature is raised to approximately 60-70° C. with the process. A control knob on the laser delivery device moves from a first to a second position to move a camera attached to the laser delivery device. The fiber optic includes a distal fiber tip extending from a malleable sheath connected to the body for delivering light energy to a treatment area.

9 Claims, 16 Drawing Sheets

(56) References Cited

U.S. PATENT DOCUMENTS

| | | | |
|---|---|---|---|
| 10,625,073 B2 | 4/2020 | Townley et al. | |
| 10,631,925 B2 | 4/2020 | Wolf et al. | |
| 11,026,746 B2 | 6/2021 | Townley et al. | |
| 11,317,970 B2 * | 5/2022 | Krespi | A61B 18/22 |
| 11,464,567 B2 * | 10/2022 | Krespi | A61B 18/28 |
| 2003/0208194 A1 | 11/2003 | Hovda et al. | |
| 2007/0005120 A1 | 1/2007 | Villacampa | |
| 2010/0057065 A1 | 3/2010 | Krimsky | |
| 2016/0045277 A1 | 2/2016 | Lin | |
| 2017/0231474 A1 | 8/2017 | Saadat et al. | |
| 2018/0103994 A1 | 4/2018 | Fox et al. | |
| 2018/0161084 A1 | 6/2018 | Newman | |
| 2018/0344411 A1 | 12/2018 | Fahey et al. | |
| 2021/0007804 A1 * | 1/2021 | Krespi | A61B 18/22 |
| 2021/0038312 A1 * | 2/2021 | Krespi | A61B 18/28 |

FOREIGN PATENT DOCUMENTS

| | | |
|---|---|---|
| WO | WO1999020185 A1 | 4/1999 |
| WO | WO2015153696 A1 | 10/2015 |

\* cited by examiner

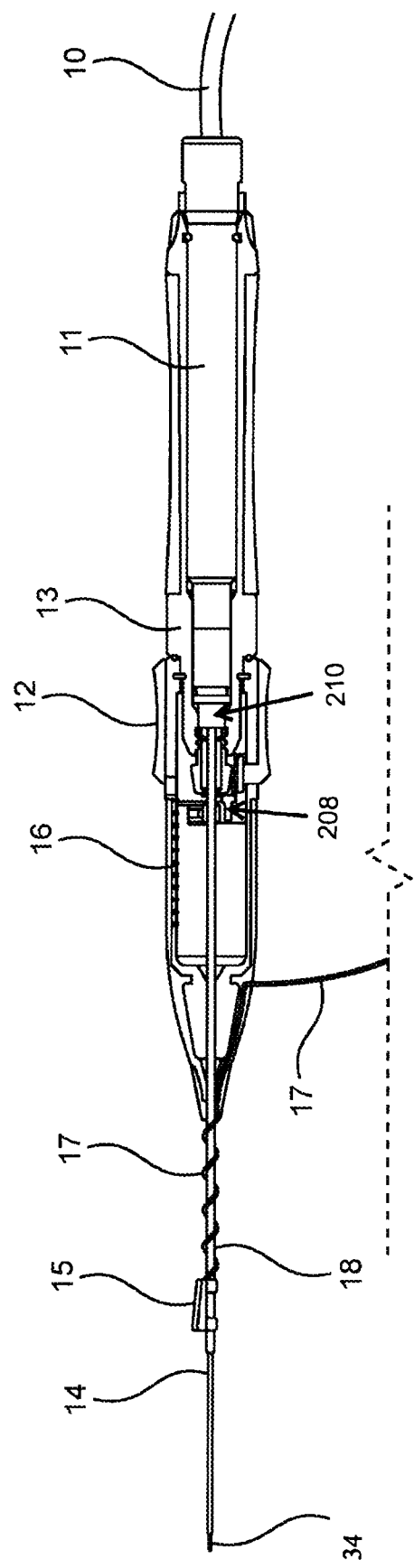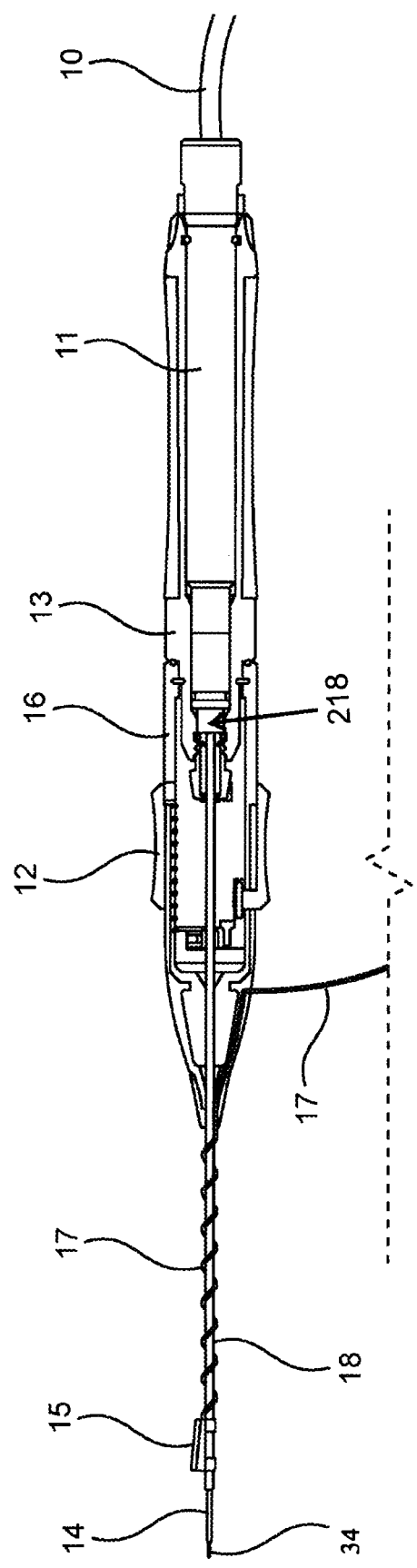

FIG. 15

Laser Tissue Interaction

| Temperature, Deg. °C | Visual Change | Biological Change - Soft Tissue |
|---|---|---|
| 37-60 °C | No visual change | Warming Hyperthermia |
| 60-65 °C | Blanching | Coagulation |
| 65-90 °C | White / grey | Denaturation |
| 90-100 °C | Puckering | Drying |
| 100 °C | Smoke plume | Vaporization |
| >200 °C | Blackening | Blackening |

Hemoglobin and oxy-hemoglobin absorption spectra, also showing emission lines of KTP laser and blue diode lasers

| Diode laser material | GaN | GaAs | InP | GaSb |
|---|---|---|---|---|
| Wavelength, nm | 380-450 | 650-1100 | 1200-2100 | 2000-3400 |
| Maximum power per emitter, W | 5 | 15 | 3 | 0.5 |

DEVICE AND METHODS OF LASER TREATMENT FOR RHINOLOGY

CROSS REFERENCE TO RELATED APPLICATIONS

This application claims benefit of and priority to U.S. Provisional Application Ser. No. 63/210,992 filed on Jun. 15, 2021 and incorporated by reference herein in its entirety.

FIELD OF THE INVENTION

The present invention relates to the field of treatment of rhinology, and more particularly to the field of laser treatment of rhinitis.

BACKGROUND

Rhinitis is defined as an inflammatory condition that affects the nasal mucosa. Its symptoms include nasal obstruction, hyperirritability, and hypersecretion. Rhinitis can be caused by a variety of different allergic and nonallergic conditions. The prevalence of rhinitis seems to have increased since the industrial revolution. One in five Americans is estimated to be afflicted with rhinitis, totaling about 60 million individuals. Allergic rhinitis is one of the most common chronic conditions in the United States. The symptoms of nonallergic rhinitis include nasal obstruction, hypersecretion, and irritability, none of which are due to allergy. Nonallergic rhinitis can be further subdivided, with vasomotor rhinitis being the most common. The symptoms of vasomotor rhinitis exacerbate with age. Allergic rhinitis may be seasonal, perennial, or both, and is characterized by sneezing, itching, rhinorrhea, and congestion. This study did focus on both allergic and nonallergic rhinitis.

Treatment is initially medical and administered via single or multi-agent, topical, systemic, or combined methods. Agents include saline irrigations, topical steroids, topical or systemic adrenergic agents, antihistamine therapy, anticholinergic agents, antileukotrienes, and combinations of these. Drawbacks include tachyphylaxis, reliable efficacy, and the need for constant daily treatment.

Multiple surgical solutions exist with varying degrees of effectiveness. Vidian neurectomy (VN), first described in 1961, was largely abandoned due to its complexity and complications that included severe bleeding from the sphenopalatine artery (SPA), crusting, cheek and palate numbness, and significant eye dryness. Although VN regained some popularity with the invention of endoscopic techniques, technical limitations with the problem of eye dryness remain present. Posterior nasal nerve (PNN) neurectomy, a modification of VN, appeared as a safer technique due to ophthalmic sparing and the fact that it targets only the posterior nasal nerve branches. Resection of the PNN reflects the physiological elimination of the parasympathetic stimulus to the inferior turbinate as induced by ipratropium, significantly improving both rhinorrhea and nasal obstruction. The induced sensory denervation further reduces secretagogue generation by reducing neurogenic inflammation. PNN resection appears to be a safe procedure that induces apparent histological changes and is sustainable for at least 48 months. Thus, selective resection of PNN can be a successful treatment for allergic and non-allergic rhinitis. PNN resection has been performed through several methods. Meticulous dissection of the SPA allows for identification of the nerve, which is found mostly posterior and inferior to the artery, usually while sparing the artery. Recently developed alternative approach targeting the lateral nasal wall mucosa without any dissection can also be applied. This can be achieved with a cryotherapy device (applied endoscopically to the posterior middle meatus) that is used to freeze the PNN region, bilaterally. Without precise identification of the nerve, cryotherapy can be done in the office, and a follow-up with patients has shown reduction in rhinorrhea and congestion for many months.

SUMMARY OF THE INVENTION

The present invention is a process and device for laser ablation of upper airway to improve air way obstruction, including, but not limited, for treating nasal valve, turbinate reduction, swell body and to ablate the posterior nasal nerve (PNN) for the treatment of rhinitis, and other rhinology and laryngology medical treatments. The diode laser delivery device with elongated fiber optic tip is inserted through a patient's oral, or nostril cavities. For the specific treatment of rhinitis, the fiber optic tip is inserted through a patient's nostril and has an ability to reach both above and under the patient's middle turbinate for treatment of both inferior and superior branches of the posterior nasal nerve. Skin and tissue temperature is raised to approximately 60-70° C. during the treatment process. Optimal treatment wavelength was found to be approximately 940 nanometers with the present invention but a blue or green visible light laser with an optimal illumination treatment wavelength of 380-450 nanometers is also used with the present invention.

The process of the present invention for the treatment of rhinitis by laser ablation of posterior nasal nerve includes ablating the posterior nasal nerve by a diode laser delivery device with an elongated uninitiated clear fiber tip. As the branches of the posterior nasal nerve are located above and below the middle turbinate of the patient, the diode laser delivery device is initially inserted through the patient's nostril and into an area of tissue near the middle turbinate. In the process of the present invention, the diode laser operates at approximately 940 nanometers. With the process, the heating of tissue by the device is done to approximately 60 to 70 degrees Celsius. The tip of the diode laser delivery device is positioned at a location above the middle turbinate. The process then ablates the lateral posterior superior branch of the posterior nasal nerve. By then positioning the tip of the diode laser delivery device at a position below the middle turbinate, the process allows the medical professional to ablate the lateral posterior inferior branch of the posterior nasal nerve. In an embodiment of the present invention, the fiber optic having a fiber tip of the laser delivery device is malleable and is adjustable and capable of configuration that is optimized to anatomical differences of individual patients. In an embodiment of the present invention, the fiber optic having a fiber tip of the laser delivery device is disposable, or reposable, meaning used for a limited number of times, for example 5 procedures, and then disposed of. In another embodiment of the present invention, the laser delivery device is re-usable. The laser delivery device for the present invention is disposable together with the fiber optic. In another embodiment the laser delivery device is reusable or reposable and the disposable fiber optic is connected to the disposable or reposable laser delivery device by removable means. The delivery device includes a disposable sheath to cover the delivery device in an embodiment.

A diode laser ablation of posterior nasal nerve (PNN) study was performed: Office based (Topical/Local Anesthesia), N=11; Ambulatory (Sedation/General anesthesia), N=21. Based on the results, there were shown: Non-allergic 15 pts (47%), Allergic 17 pts (53%). In ASU, when anatomy does not permit endoscopic access, there is benefit of the present invention. There are the added benefits of short treatment time, and a smaller area being treated. It is well tolerated by patients with rapid healing, and no crusting.

The 940 nm diode laser ablation thermal profile is used with the present invention. Using a clear tip fiber in non-contact mode, tissue temperature is raised to 60-70 C maximum to achieve very superficial mucosal blanching and ablate the PNN located adjacent to, and along the blood vessels just under the mucosa. By keeping temperature under 70 C denaturation is achieved, which is partially reversible and may be early coagulation, (never vaporization).

With the present invention the advantages of 940 nm diode laser with clear fiber tip are shown. This wavelength is optimal wavelength for ablating mucosal surface and provides controlled tissue heating. The fiber optic with the clear fiber tip in non-contact mode blanches the mucosa selectively effecting the nerve in sub-mucosa without effecting adjacent mucosa. There is minimal crusting and swelling with the present invention and it provides an improved method by avoiding collateral ablation, and instead targeting the two zones in the back of the nose, where the lateral inferior and lateral superior branches of the PNN are located.

In an embodiment, there is a process for the treatment of rhinitis by laser ablation of the posterior nasal nerve which comprises ablating the posterior nasal nerve by a diode laser delivery device with an elongated fiber optic with a clear fiber tip, where the branches of the posterior nasal nerve are located, above and below the middle turbinate. The fiber optic with the fiber tip of the diode laser delivery device is inserted into an area of tissue near the middle turbinate with the diode laser delivery device operating at approximately 380 to 450 nanometers—a blue laser process. The physician positions the tip of the fiber optic of the diode laser delivery device at a position above the middle turbinate. The process heats the tissue to approximately 60 to 70 degrees Celsius ablating the lateral posterior superior branch of the posterior nasal nerve. The physician then positions the fiber tip of the fiber optic of the diode laser delivery device at a position below the middle turbinate. Then, the process ablates the lateral posterior inferior branches of the posterior nasal nerve.

In an embodiment of the blue laser process, the fiber optic of the laser delivery device may be malleable. In an embodiment of the blue laser process, the fiber optic with the fiber tip of the laser delivery device is adjustable and capable of configuration which can be optimized to anatomical differences. In another embodiment of the blue laser process, the fiber optic with the fiber tip is disposable. In an embodiment of the blue laser process, the laser delivery device is re-usable. In yet another embodiment, the laser delivery device is disposable or reposable. In an embodiment, the fiber optic with a fiber tip is connected to the disposable laser delivery device by removable means. In another embodiment of the blue laser process, the laser delivery device includes a disposable sheath to cover the laser delivery device.

The process, in another embodiment, further comprises selectively ablating blood vessels with a blue laser in a non-contact or contact coagulation mode. In an embodiment, the process includes wherein the laser delivery device operating at approximately 380 to 450 nanometers.

With the present invention, there is a laser delivery device which comprises a handle body with a proximal end and a distal end, where the body includes a handpiece section connected with a front section. The handpiece section has an opening at the proximal end of the body with an internal cavity extending from the opening and ending at a cavity base with the cavity configured to receive and connect with an optical module through the opening of the handpiece section. Fiber optic is attached to the laser delivery device by having a proximal end of the fiber fixed to the cavity base inside the cylindrical body in a manner to receive laser energy from the optical module when the optical module is in use. The fiber optic extends from the cavity base through the remaining length of the body to and through a distal end of the body. The fiber optic has a sheath, preferably metallics, covering the fiber optic and connected to the cavity base with the fiber optic. The present invention includes a control knob on the body capable of moving from a first position to a second position along the body, and the control knob is mechanically connected to a tube on the sheath internal to the body. The tube and the sheath with the fiber optic extend through the distal end of the body. A mini video camera is positioned on the tube external to the body, where the camera and the tube move from a first camera position to a second camera position when the control knob is moved from a first position to a second position. The fiber optic has a distal tip extending from the sheath for delivering light energy to the treated area and by moving the mini video camera, the medical professional has the ability to adjust the field of view of the treatment area. Additionally, the fiber optic with a fiber tip of the laser delivery device is malleable and adjustable and therefore capable of configuration and optimized to anatomical differences of treatment areas for different procedures and patients.

In an embodiment, the laser delivery device further includes the control knob rotating the front section of the body. In an embodiment, the laser delivery device delivers the laser beam at approximately 940 nanometers when connected with the optical module, (from the operating laser console). In embodiments, the laser delivery device includes where the fiber optic with a fiber tip is disposable, and the laser delivery device is re-usable, reposable or disposable.

The present invention includes a process for treatment of rhinitis by laser ablation of posterior nasal nerve which comprises ablating the posterior nasal nerve by a laser delivery device with a fiber optic with a fiber tip, with the laser delivery device having a body with a proximal end and a distal end, and the body including a handpiece section connected with a front section having an opening at the proximal end. The handpiece section has an internal cavity extending from the proximal opening and ending at a cavity base, with the cavity configured to receive and connect with an optical module through the opening of the handpiece section. The laser delivery device used with the process includes fiber optic having a proximal end fixed to the cavity base inside the body in a manner to receive laser energy beam from the optical module when the optical module is inserted into the handle cavity and in use. The fiber optic with a fiber tip extends from the cavity base through a distal end of the body with the fiber optic having a sheath covering the fiber optic and connected to the cavity base. A control knob on the body capable of moving from a first position to a second position, with the control knob connected to a tube on the sheath internal to the body, where the tube and the sheath with the fiber optic are extending through the distal end of the body. The process includes a camera positioned on the tube external to the body, with the camera and the tube moving from a first camera position to a second camera position when the control knob is moved from a first position to a second position. The fiber optic has the fiber tip extending from the sheath for delivering laser energy beam to a treatment area, such as the posterior nasal nerve located above and below a middle turbinate. In the process, the fiber optic of the laser delivery device is inserted into an area of tissue near the middle turbinate, with the laser delivery device delivering a wavelength for therapeutic treatment. The process includes heating the tissue to approximately 60 to 70 degrees Celsius and positioning the fiber optic of the laser delivery device with its fiber tip at a position above the middle turbinate. Then, the process includes the step of ablating lateral posterior superior branches of the posterior nasal nerve and positioning the fiber tip of the fiber optic of the laser delivery device at a position below the middle turbinate. The process then includes ablating lateral posterior inferior branches of the posterior nasal nerve.

In an embodiment, the process further includes where the control knob of the laser delivery device rotates the front section of the body. In an embodiment, the process includes the fiber optic with a fiber tip of the laser delivery device being malleable. In an embodiment, the process further comprises wherein the fiber optic with a fiber tip of the laser delivery device is adjustable and capable of configuration to anatomical differences.

In an embodiment, the process of the invention includes where the laser delivery device delivers a laser energy beam of approximately 940 nanometers when connected with the optical module. In embodiments, the process includes where the fiber optic with a fiber tip of the laser delivery device is disposable and also where the laser delivery device is re-usable, reposable, or disposable.

BRIEF DESCRIPTION OF THE DRAWINGS

Some embodiments of the invention, and of making and using the invention, as well as the best mode contemplated of carrying out the invention, are described in detail below, by way of example, with reference to the accompanying drawings, in which like reference characters designate like elements throughout the several views, and in which:

FIG. 5 is the delivery device of the present invention illustrating the internal components with optical module and with camera in a first position.

FIG. 6 is the delivery device of the present invention illustrating the internal components with optical module and with camera moved to a second position.

FIG. 15 is a general reference chart of laser tissue interaction of temperature, visual change and biological change.

DETAILED DESCRIPTION

Figure 1:
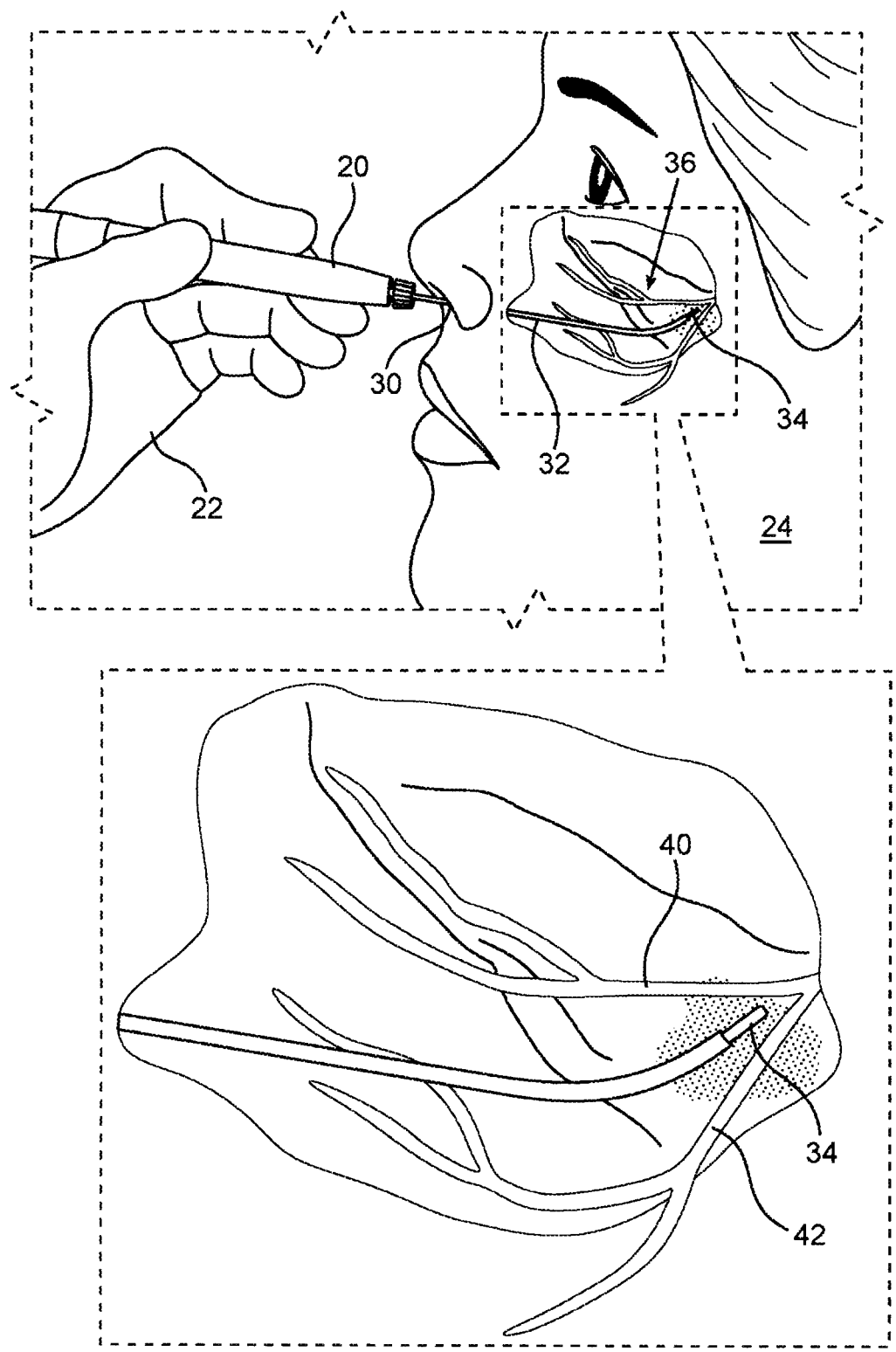
FIG. 1 illustrates a procedure of the present invention, and includes an exploded view.

The present invention shall be described with reference to the included Figures and charts. FIG. 1 illustrates the process of treatment of rhinitis. In FIG. 1 there is shown laser ablation of posterior nasal nerve (PNN), with the treatment of lateral posterior superior branch of the PNN. The illustration includes a patient 24 and a medical professional 22 holding the diode laser delivery device 20 for delivery of treatment to the patient. The handheld laser delivery device 20 with elongated and needlelike insertion section or neck 32 culminating in fiber tip 34 is inserted through the patient's nostril 30 with the fiber tip 34 of the fiber optic 32 extending into the area of the patient's middle turbinate 36. In the area of the middle turbinate, there are two main branches of the PNN indicated by the set of branched lines extending from a common point. One nerve (superior branch) 40 is located above the middle turbinate and one nerve (inferior branch) 42 is located below the middle turbinate. In FIG. 1, the fiber tip 34 of the needlelike insertion neck section 32 of the diode laser delivery device 20 is below the middle turbinate 36. The lateral posterior branches 40 and 42 are treated in this manner.

The diode laser treatment is performed with a laser beam with a wavelength of approximately 940 nanometers that raises the skin/tissue temperature to between 60 and 70° C. It is important to try to perform this laser treatment without crusting the surface of the tissue.

The diode laser delivery device in this process is able to reach for treatment both branches 40, 42, as opposed to radio frequency (RF) and cryo-technology based treatments, which are only able to treat the inferior branch and result in a wider collateral ablation due to the significantly larger size delivery tools used in RF and cryo-technology treatment processes.

The elongated fiber optic includes a malleable sheath that allows the medical professional to bend and adjust the shape of the distal section of the fiber optic 32 and its fiber tip 34 for anatomic differences. With the present invention, the fiber optic of the laser delivery device is malleable and or made of a malleable material. The fiber optic of the laser delivery device with its fiber tip is adjustable and capable of configuration which can be optimized to anatomical differences for each individual patient. The laser delivery device together with its fiber optic is disposable, or the laser delivery device is reposable with the disposable fiber optic connected to the laser delivery device by removable means, such as fasteners, clips, mechanical methods, adhesives. Alternatively, the fiber optic is disposable, and the laser delivery device is reusable with the fiber optic connected to the disposable laser delivery device by removable means, such as fasteners, clips, mechanical methods, adhesives. The laser delivery device may also include a disposable sheath to cover the laser delivery device.

Figure 2:
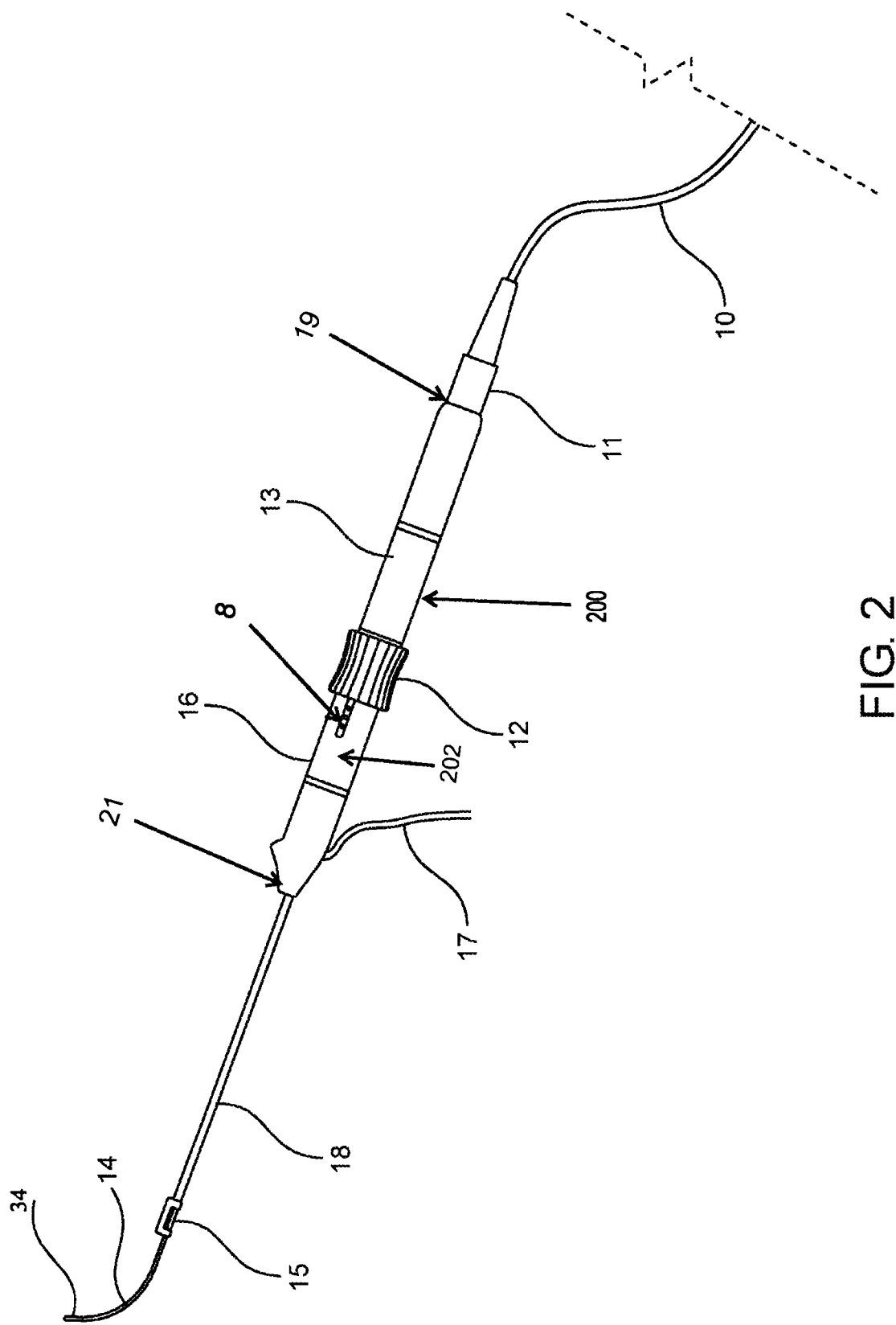
FIG. 2 is the delivery device of the present invention.

Referring to FIG. 2, there is shown the laser delivery device for use with the present invention. In FIG. 2, with the laser delivery device of the present invention, which is a pen like or wand shaped device optionally with a generally cylindrical body 200 having a proximal end 19 and a distal end 21 of the body 200. Extending from the distal end 21 of the body 200 is tube 18 which covers a malleable sheath 14, through which the tip of the fiber optic 25 extends beyond the sheath 14 as the fiber tip 34. Together, this forms the needlelike insertion neck 32 noted above in FIG. 1. A mini video camera 15 is attached to the tube 18 on the sheath 14. The device shown in FIG. 2 includes the laser optical module 11 connected to the trunk fiber 10 and inserted into the proximal end 19 of the body of the laser delivery device 20, which is connected to a laser system console (not shown). The laser optical module 11 is a reusable optical module that delivers the laser energy beam generated by the laser system console, into the laser delivery device and through the fiber optics 25 to the fiber tip 34 at the distal end of the laser delivery device 20. The fiber tip 34 protrudes from within a malleable sheath 14, which is partially covered by and inside of flexible tube 18 at the distal end 205 of tube 18. The tube 18 is preferably a polymer material, such as a polyamide material, but other materials known in the art may be used. The fiber optic 25 is contained within the rigid yet malleable sheath 14 (which is inside of tube 18) and inside the laser delivery device 20 where the fiber optic 25 has a proximal end fixed 212 inside handpiece 13 (See, FIGS. 3-6). Also shown on the laser delivery device 20 is the camera control knob 12, which is linked to and connected with video camera 15 by the tube 18. The camera control knob 12 is part of the front section 16. The camera control knob 12 can be rotated by the user around the axis of the laser delivery device 20 and rotate the front section 16. The knob 12 also slides forward and back by the user along the axis of the laser delivery device 20 by means of a slot 8 on the surface 202 of the laser delivery device 20, which is above and encasing the tube 18 and fiber. In this manner, the movement of the camera control knob 12 controls the mini camera 15 movement for rotation around the tube 18 and for also slide forward and backward along the tube 18 for changing the views and providing different views of the treatment area. The front portion of the laser delivery device handpiece is indicated by 16 and the camera cable 17 is also shown in FIG. 2.

The portion of the device held by the user comprises the handpiece or handle 13 and a front housing section 16, which may be disposable. The handpiece 13 is a stationary piece and together with the front housing section 16 and knob 12 are linked to and connected with the camera 15. The front housing section 16 rotates relative to the handpiece section 13, and hence rotates tube 18 together with the camera 15 around sheath 14. The control knob 12 fixed on the outer surface of front housing section 16 is connected internally to the tube 18 at the tube proximal end 214 by mechanical connection, such as a pin or screw, which can also act to hold the proximal end of tube 18 in place. The fiber optic 25 and sheath 14 continue to extend internally along the device axis and are permanently fixed internally to the disposable housing at the location of the fiber optic and sheath proximal ends 212 and 216. Prior to a medical procedure or examination or treatment, the physician or medical professional 22 inserts, plugs or attaches the laser optical module 11 into the laser delivery device through the proximal opening 9 (shown already attached in FIG. 2). Internally, the device assures the reliable optical interface and link between the fiber optic 25 and the laser optical module 11 at internal optical interface connection 210, and prevents loss of light energy at the connection point between the laser optical module 11 and the fiber optic 25. After the connection, laser light travels from the laser optical module 11 through the length of the fiber optic 25 to the fiber tip 34.

The laser fiber 25 allows for the laser light energy to be emitted from the distal tip of the laser fiber 34. This is accomplished by the laser beam that is generated in the laser system console guided through the trunk fiber 10 to the laser optical module 11 all the way through the length of fiber optic 25 of the laser delivery device 20 until reaching the fiber tip 34. The laser fiber 25 is fixed to an interior part of and within the disposable handpiece housing 13. The distal end 218 of the re-usable laser optical module 11 is connected tightly to the proximal fiber optic end 212 of the fiber optic 25 inside the disposable handpiece housing 16 to minimize laser energy losses. The laser energy propagates from the fiber inside the proximal end 212 of the fiber optic 25 along the fiber optic 25, which is inside sheath 14, all the way to its distal tip 34 where the laser is emitted to the treated tissue. The sheath 14 is rigid yet malleable for an easier navigation and access to hard-to-reach anatomies during a medical procedure.

The present invention is designed as a laser delivery wand shaped device that is intended to be disposable, optionally reposable or optionally reusable. The laser delivery wand comprises at least the above two main components—the main handle/handpiece 13 and the front section 16, and the needlelike insertion neck 32 comprises at least sheath 14 covering the fiber optic 25 of about 200-500 micron diameter and may be set in various lengths typically 40 mm to 300 mm. Optionally the needlelike insertion neck 32 includes over sheath 14, a tube 18 with a mini camera connected to it.

A diode laser generator unit/system console (not shown) is generating a laser beam, at about 940 nm, and also an option of about 440 nm for use with the present invention, although other ranges of wavelength are within the scope of the invention. The diode laser generator unit has an umbilical cord/trunk fiber 10, which connects at the distal end with the laser delivery device with a laser optical module 11.

The distal end 218 of the optical module 11 is interfaced optomechanically with the proximal end of the fiber optic 25 of the laser delivery device. The fiber optic 25 delivers the laser energy beam that is emitted from the distal end 218 of optical module 11 through the fiber tip 34 to the tissues. The shape of the malleable sheath 14, from which the fiber tip 34 extends, and contains the flexible fiber optic 25, can be adjusted to adhere to different anatomies. The fiber tip 34 can deliver the laser energy in at least three different modes of tissue interaction, including (i) non-contact, by 'hovering over' the mucosa and heating it superficially; (ii) contact, by applying the energy superficially by contacting the mucosa; and (iii) interstitial, by puncturing through the tissue and delivering the energy into the tissue.

In an embodiment, an optional device feature can have the imaging module of a mini camera 15 that comprises an imaging sensor (around 1 mm×1 mm, typically CMOS) and illumination means, which are all mounted in a camera housing. The illuminating means includes a light guiding or emitting means such as fiber optic or at least one, or multiple LEDs. The imaging module is connected to the needlelike insertion neck 32 by being mounted/latched onto the tube 18 in at least one point. The imaging module together with the tube 18 have ability to slide back and forth along the needlelike insertion neck 32 by sliding the camera control knob 12 from a first point to a second point. The imaging module can also be rotated around the fiber optic and sheath 14 by rotating the camera control knob 12. An electrical cable 17 is connected between the proximal end of the imaging module and an electronic circuitry unit (camera control unit) that provides power to and controls the imaging module and converts its returning signal to a video signal, which is used as input to a video display.

Figure 3:
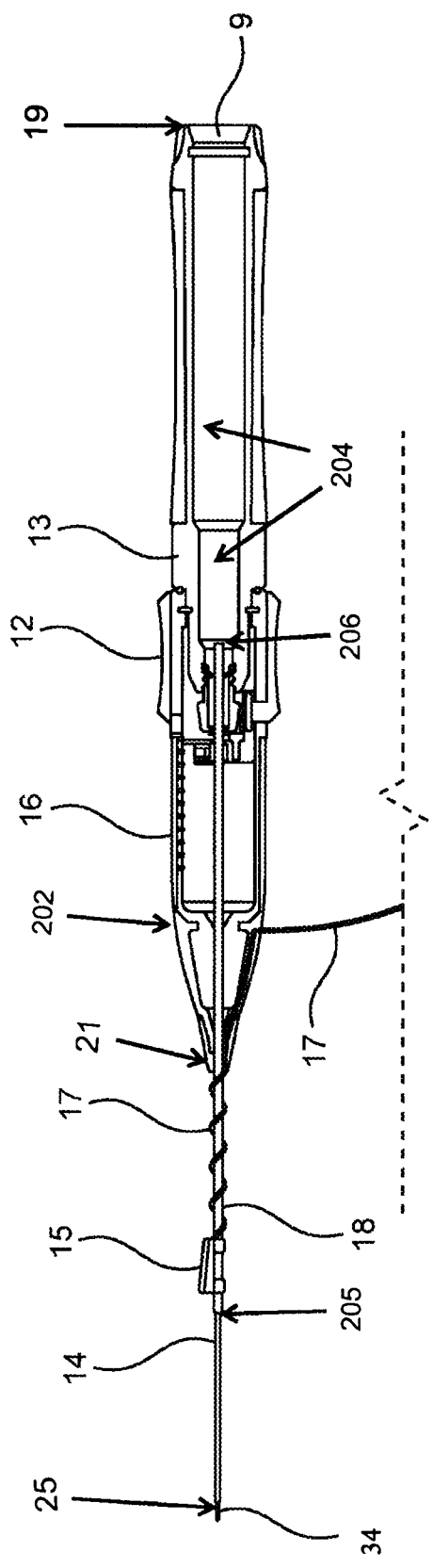
FIG. 3 is the delivery device of the present invention illustrating the internal components without optical module, and with camera in a first position.

Referring to FIG. 3, there is shown the present invention with the internal view of the various elements of the device. In FIG. 3, there is seen the device 20 with an opening 9 at the proximal end 19 for receiving laser optical module 11 which is at the distal end of the trunk fiber 10 (FIG. 2, FIG. 4) within a shaped cavity 204 of the internal volume in the back portion of the device. The shaped cavity 204 is configured and shaped to receive and fit the optical module 11. At the base 206 of shaped cavity 204, there is an optical connection 210 that is designed to interface with the proximal end of the fiber optic 25 with minimal optical losses. The disposable laser delivery device (the handpiece) 20 includes a back handheld section 13, the front section 16 with the camera control knob 12. The camera control knob 12 is a rotatable ring like structure around the outer surface 202 of the laser delivery device 20, with a connecting piece 208 fastened to the inner sheath 14 (rigid and malleable) and tube 18 (preferably composed of polymer material for flexibility). Turning the knob 12, moves the connecting piece 208, which rotates the outer tube 18 of the needlelike insertion neck section 32 and likewise, rotates the camera 15 which is fastened to the tube 18 external to the handpiece unit 13 and 16, and connected via camera cable 17 to an electronic camera control unit and to a video display (not shown).

Contained within the disposable handpiece back section 13 is the internally shaped cavity 204 for receiving the laser optical module 11 which when inserted through the opening 9, connects with the laser system console (not shown) through the trunk fiber 10. Connected to the front section 16 is the flexible outer tube 18 which can be slid and rotated over the sheath 14 that encapsulates the fiber optic 25 that are connected to the back section of the handpiece 13, and together extends through the forward length of the handpiece to emerge from a distal end 21 of the handpiece. The imaging module is fixed to the distal end of the polymer tube 18. The proximal end of the polymer tube 18 is connected to the camera control knob 12 by the connection piece 208.

Figure 4:
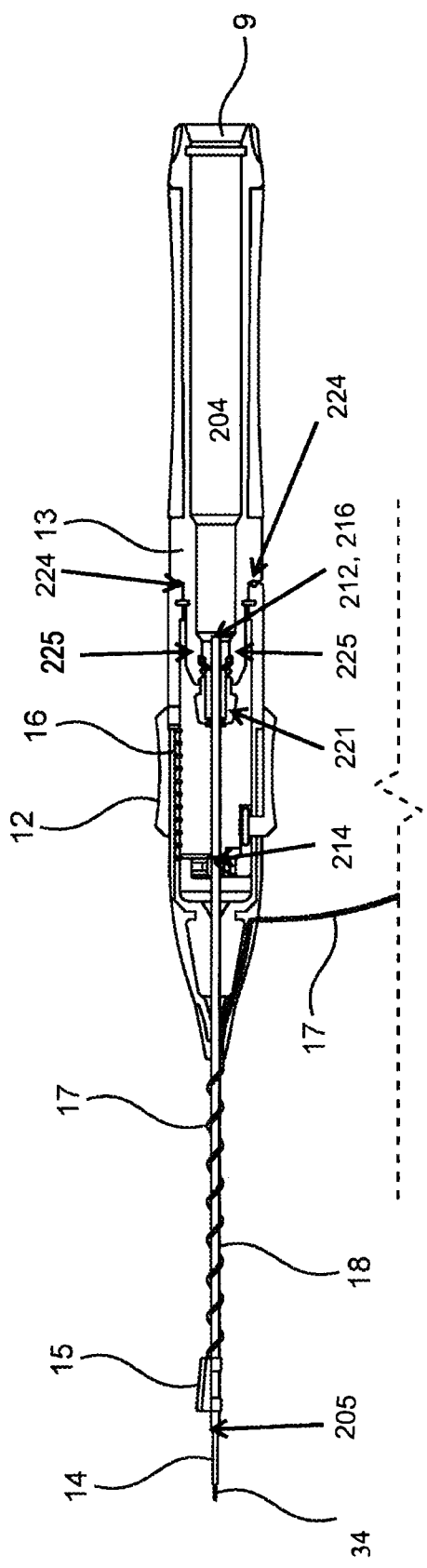
FIG. 4 is the delivery device of the present invention illustrating the internal components without optical module, and with camera moved to a second position.

In an embodiment, the front section of the handpiece 16 is rotatable by the user and can rotate the tube 18, around the fiber optic 25 and its malleable sheath 14. This allows for camera 15 on the tube 18 be rotated up to 360 degrees around the central axis of the needlelike insertion neck 32 for visual access to the medical procedure and tissue area. With reference to FIG. 4, there is shown the back handpiece section 13 having internal female type connection 225 for receiving and securing the proximal connector of the fiber optic 25 and its malleable sheath 14, shown as 221, at proximal end of fiber optic and malleable sheath. The connection 225 may also be a snap-fit, thread or other mechanical type fasteners. The back handpiece section 13 has a rotation connection surface 224 which contacts the housing section 16 and allows the front (distal) handpiece section 16 to rotate relative to back handpiece section 13 when the sections are connected. The rotation connection surface 224 may be designed as including, but not limited to, an O-ring, washer or mini ball bearing contacts.

As seen in FIG. 3, the device is shown with the camera control knob 12 in a first position, as a resting or locked position. In FIG. 4, there is shown the present invention with a second position for the camera control knob 12 (See, FIG. 4) as the user has moved the camera control knob 12 forward along slot 8. The control knob 12 with connection piece 208, such as a pin or screw, fastened to the tube 18 which is placed over the sheath 14 (which contains the fiber optic 25) and moves the tube 18 forward together with the mini camera over the sheath 14 to a second position. This action moves the camera 15 closer to the fiber tip 34, allowing for close up observation and views of the treatment area when the device is in use on a patient. By rotating the knob 12, tube 18 with the camera 15 are moved to various positions in up to 360 degrees range of motion around the metal sheath 14 acting as an axis.

In FIGS. 5 and 6, there is shown the present invention device with the laser optical module 11 with trunk fiber 10 attached in place, through back opening 9 on the proximal end 19. The laser optical module 11 is placed into the shaped cavity 204 contained inside the back handpiece section 13. In this manner, the laser energy is delivered into the device and to the laser fiber optic 25. Also, in FIG. 5, the camera control knob 12 is shown in a first position, and in FIG. 6, it is shown in a second position, which moves the camera/imaging module 15 forward along the axis of the needlelike insertion neck 32 to a position which is desired by the medical professional for imaging in the treatment area.

In an embodiment, the needlelike insertion neck comprises the fiber optic 25, encapsulated inside a malleable sheath 14. A small portion of the fiber optic extends beyond the sheath and forms the fiber tip 34. The fiber optic with its sheath, optionally a malleable sheath, are fixed to the handle and are not rotating with the camera control knob. Onto the sheath 14, is slid a polymer, flexible tube 18 that the image module 15 is attached to at the distal end of the tube. This distal end is shorter than the sheath 14. The tube 18 which rides over the sheath 14 is connected to the camera control 12. Moving the camera control knob moves, rotates and/or slides the tube 18 together with the camera 15 which is connected to it. The tube 18 is flexible to adhere to the shape which may be given to the malleable sheath 14.

The laser fiber used in the present invention has a diameter range of 100 microns to 200 microns, and the metal sheath 14 covering the fiber is bendable with up to 70 degrees curvature. The fiber optic can be attached by the medical professional or pre-assembled to the laser delivery device hand piece and then shaped and sized appropriately for a particular medical procedure, examination or surgical site. The present invention with the imaging module 15 substitutes as a replacement for conventional rigid, or flexible endoscopes. Overall, the handpiece is manufactured from materials known in the arts, including but not limited to, molded plastic parts, and it is assembled by manufactured methods known in the art.

The present invention of a mini camera integrated or coupled to and in use with a power unit or power tool provides numerous advantages over present power tools and medical equipment, by eliminating the need for an external rigid or flexible endoscope that is currently required for providing the physician with direct visualization of the treated area. In addition, the device of the present invention can be used with robotic assisted surgery by having the robotic clamp grip the laser delivery device and the camera control knob 12. Additional medical procedures which are aided by navigation techniques can be used with the present invention. For example, CT scans can provide surgeons with navigation points within the human body. With the present invention, navigation sensors can be included inside the device or on or about the distal tip 34. Techniques such as adding inductors or metal coil to the tip of the needlelike insertion neck and using magnetic field and imaging to triangulate the fiber tip may also be employed with the present invention.

In order to determine the optimal methods with the present invention, a comparison of diode laser wavelengths 810, 940 and 980 nm for both clear tip and black tip delivery was analyzed. The results provide a visualization of thermal distribution in biological tissues and a comparison effect of tissue chromophores. The comparison involved tissue with high blood content (dark liver was used) and low blood content (pale pork muscle was used).

Figure 7:
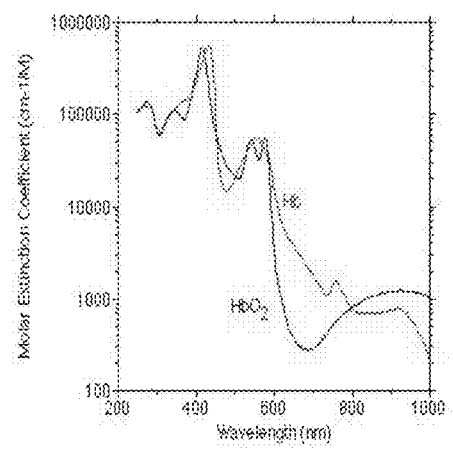
FIG. 7 is a chart of the absorption chromophores molar extinction coefficient vs. wavelength.
Figure 8:
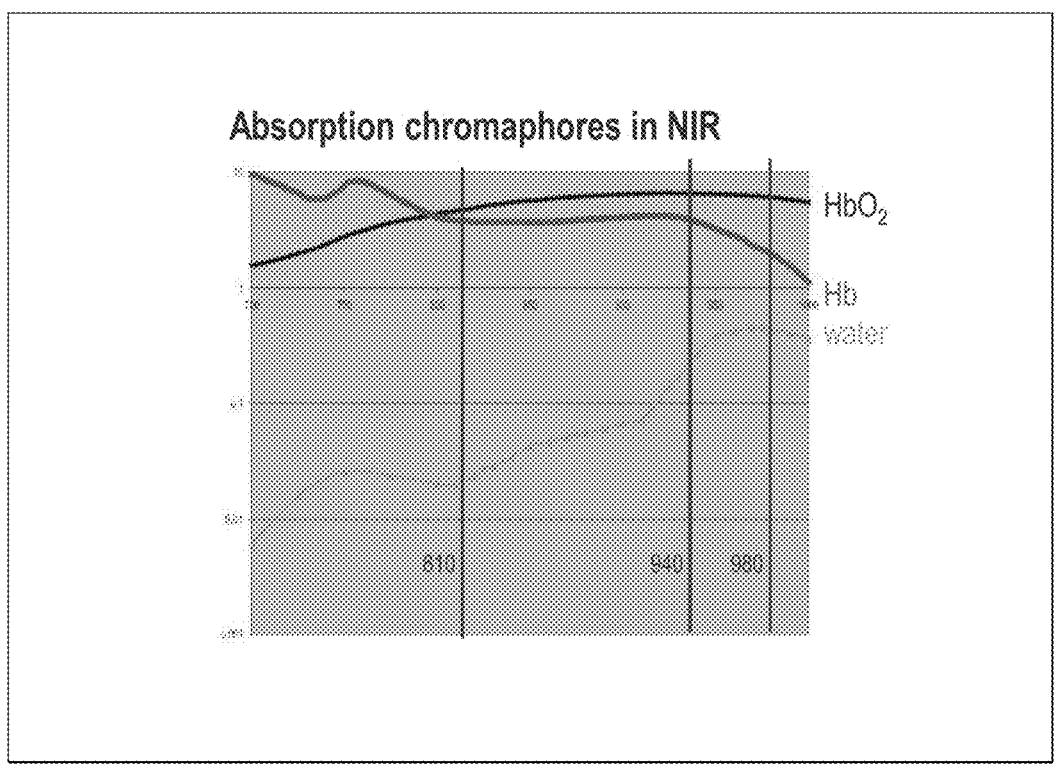
FIG. 8 is a chart of absorption chromophores in NIR.

FIGS. 7 and 8 illustrate the absorption chromophores of Hb and $HbO_2$, with the wavelengths of 810 nm, 940 nm and 980 nm indicated in FIG. 8.

Figure 9:
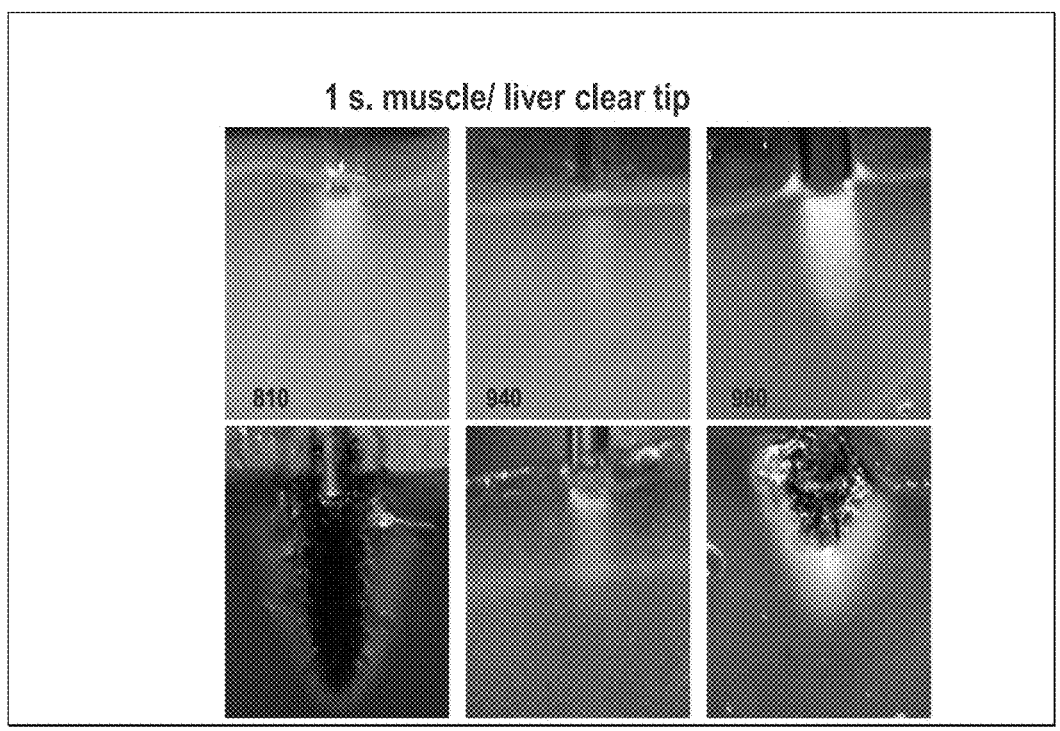
FIG. 9 illustrates 1 second of treatment with clear tip laser device at various wavelengths.
Figure 10:
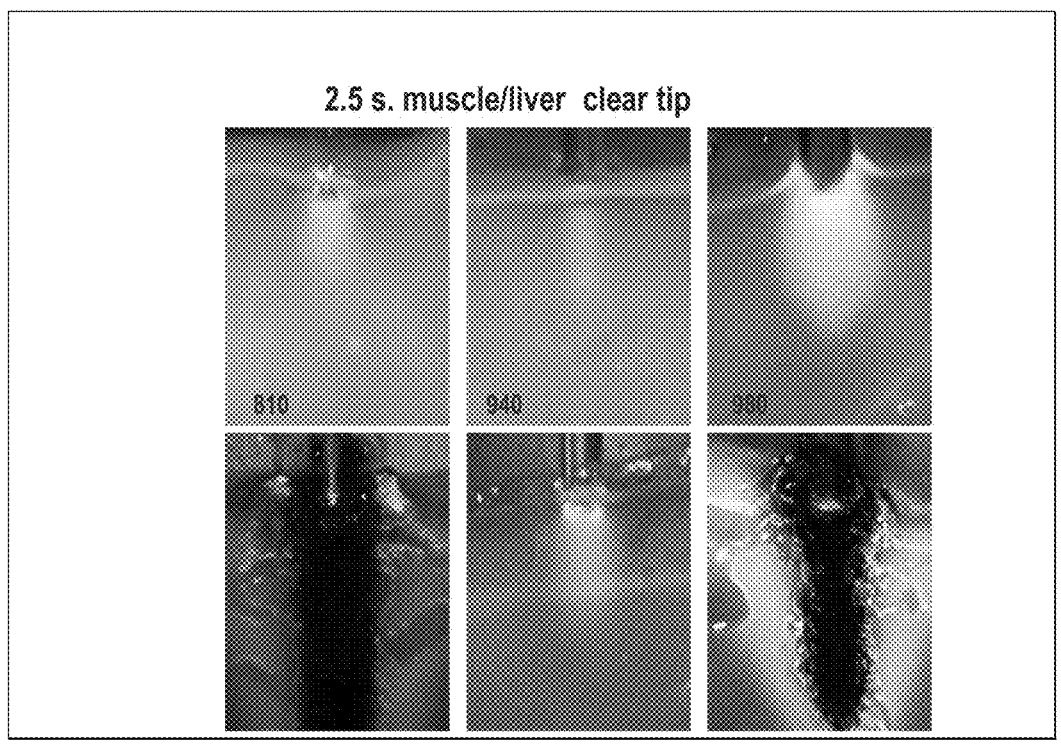
FIG. 10 illustrates 2.5 seconds of treatment with clear tip laser device at various wavelengths.
Figure 11:
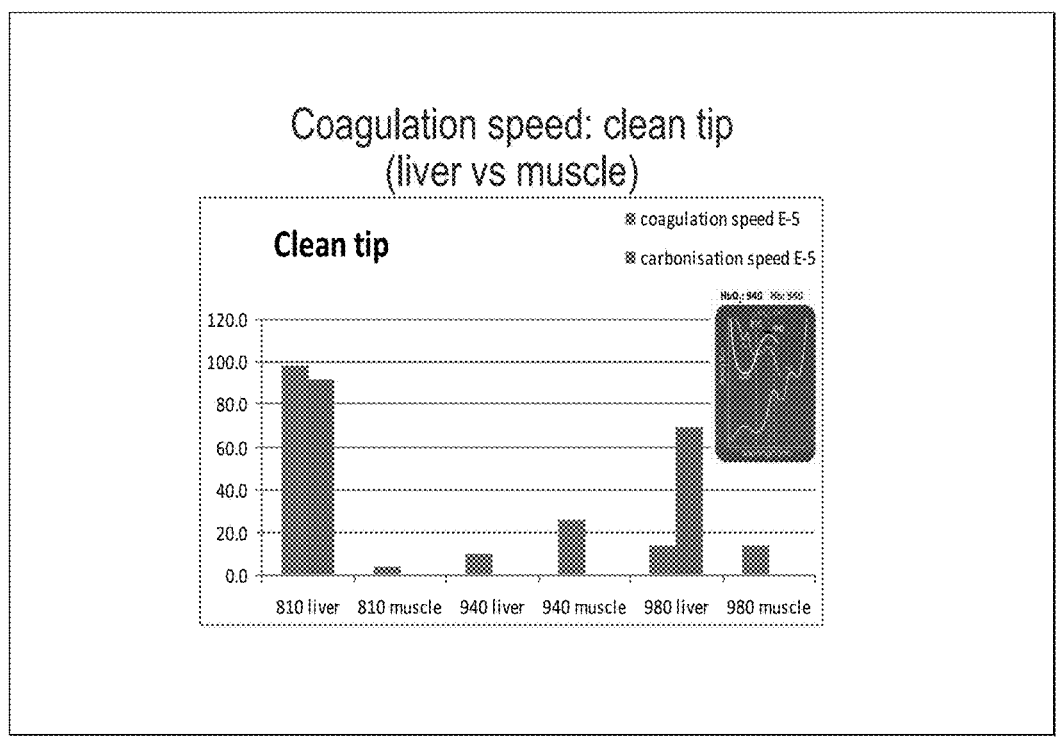
FIG. 11 is a chart of coagulation speed with the clean/clear tip laser device.

With FIGS. 9, 10, and 11, there is shown the effects of the clear tip technique which is used with the present invention. FIG. 9 illustrates one second treatment of muscle tissue (top row) and liver tissue (bottom row) with clear tip treatment. The results are shown for 810, 940 and 980 nm, with 940 nm indicating no destruction of tissue. Similarly, FIG. 10 illustrates 2.5 second treatment of muscle (top row) and liver tissue (bottom row) with a clear tip delivery device. Again, the results are shown for 810, 940 and 980 nm with 940 nm indicating no destruction of tissue. FIG. 11 indicates the coagulation speed with the clean tip for liver and muscle tissue at each of the wavelengths of 810, 940 and 980 nm.

Figure 12:
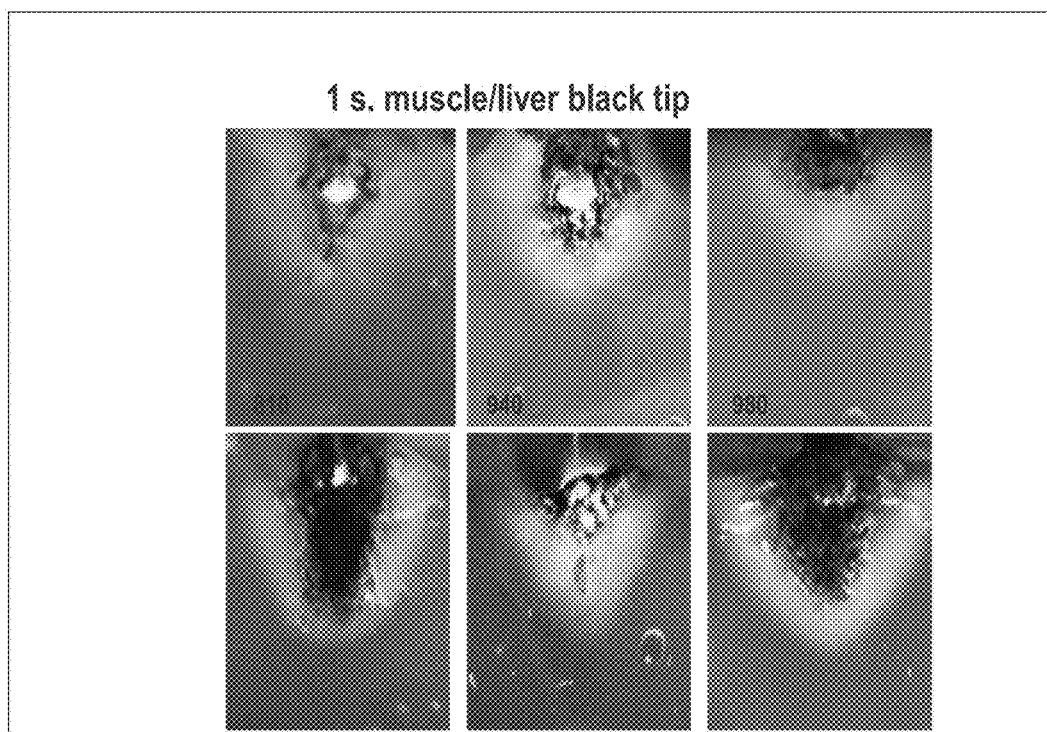
FIG. 12 illustrates 1 second of treatment with a black tip laser device with undesirable results.
Figure 13:
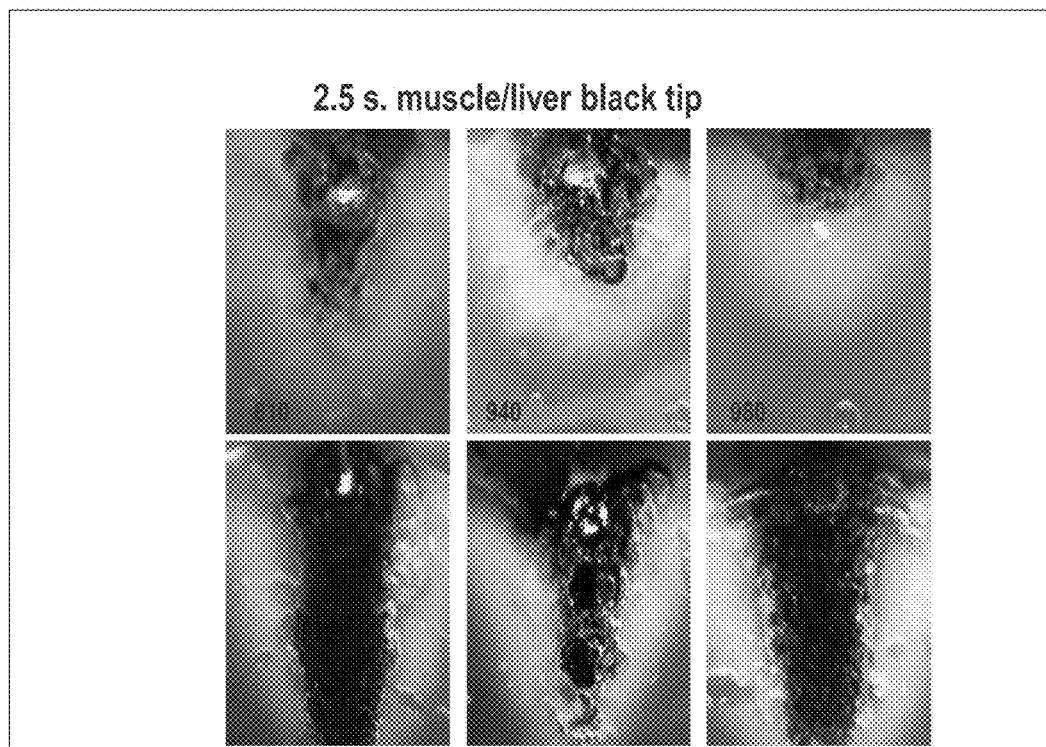
FIG. 13 illustrates 2.5 seconds of treatment with a black tip laser device with undesirable results.
Figure 14:
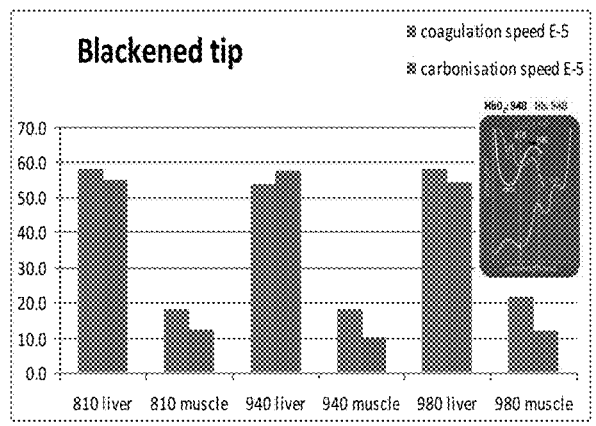
FIG. 14 is a chart of coagulation speed with the black tip laser device.

With FIGS. 12, 13, and 14, there is shown the undesirable effects of the delivery system using the black tip technique as it destroys tissue. This is shown with FIGS. 12 and 13 respectively as images of damaged tissue with 1 second treatment (FIG. 12) and 2.5 seconds treatment (FIG. 13) across a range of wavelengths 810 to 980 nanometers for each treatment. FIG. 14 indicates the coagulation speed with the blackened tip. FIG. 15 is a table of the laser tissue interaction with temperature, visual change, and biological change indicated in the respective columns.

The observations are reproducible in series (3 times). The high Hb absorption at 810 nm is higher than theoretical expected as compared to 940 and 980 nm. The tissue effect at 940 nm seems to be less dependent on the presence of chromophores compared to that at 810 and 980 nm for a controlled coagulation effect. The 940 nm diode laser shows to have a controlled coagulation/sterilization effect less dependent on the presence of blood. For 810 nm and 980 nm diode lasers initiate tissue carbonization and ablation within a few seconds depending on the presence of chromophores (especially blood). The pre-coated 'black tip' is very efficient for instant ablation of tissue within 1 second.

The 940 nm diode laser has a wavelength allowing for controlled submucosal thermal penetration. The diode laser is used in both vein ligation and neural tissue ablation through a non-contact (not initiated) type tip. As the vessel ablation requires power settings around 12 W, and nerve/brain tissue ablation is induced at 6 W, a power setting of no more than 5-6 W is sufficient for ablating the endonasal nerves. If the laser's heat is maintained above a certain threshold temperature at which proteins begin to denature, the tissue irreversibly coagulates and the tissue's optical properties (most significantly, the absorbance properties) change. This is easily monitored by observing the properties of the nasal mucosa, as overheating may produce vaporization and carbonization, at temperatures 100-300C which are not desired.

Armed with data generated from bench experiments and learning from various disciplines, such as testing diode laser exposure on tissue using clear (non-initiated) and black (initiated) fiber tips with various power densities, the 940 nm laser's potential as a tool in PNN ablation was explored. Overall, it is shown that the diode laser delivery at 940 nm is the best wavelength to ablate and safely coagulate without deep penetration and minimal lateral tissue necrosis. A range of wavelengths around the 940 nm, slightly greater and slightly less similarly provides the results.

The non-contact ablation method with un-initiated fiber tip (Clear tip) at around 4-5 W, gives the best and safe results for superficial tissue ablation.

With the present invention, the following clinical study has been performed:

Design Prospective, non-randomized
Population Healthy patients with rhinorrhea and nasal congestion who failed medical therapy
Primary Endpoint Total Nasal Symptom Score (TNSS) at Baseline, 30, 90 days post treatment
Scoring Scales TNSS, validated symptom scale
  Four nasal symptoms. Rhinorrhea, Nasal obstruction, Nasal itching, Sneezing
  0-3 point scale
  0=Absent symptoms
  1=Mild symptoms
  2=Moderate symptoms
  3=Severe symptoms
Results: Feasibility and Safety There were 31 patients, with 30 and 90 days follow up received from 30 patients. For feasibility, there was an ability to complete the procedure in 96% of the cases. There were 10 in the office, 21 in the ASU due to anatomical access. Topical and/or local anesthesia was used in the office. The average pain score was 1.8 (scale of 0-10). For safety: there was no laser related events, no bleeding, and no crusting, headaches, facial pain or ear blockage.

Results: Efficacy
Symptoms Score 30 Days:
  55% improvement in TNSS
  Mean score 7.1 (out of 12) at baseline, reduced to 3.2
  48% improvement in Rhinorrhea
  Mean score 2.3 (out of 3) at baseline, reduced to 1.2
  53% improvement in Congestion
  Mean score 2.1 (out of 3) at baseline, reduced to 1.0
Symptoms Score 90 Days:
  51% improvement in TNSS
  Mean score 7.1 (out of 12) at baseline, reduced to 3.5
  44% improvement in Rhinorrhea
  Mean score 2.3 (out of 3) at baseline, reduced to 1.3
  48% improvement in Congestion
  Mean score 2.1 (out of 3) at baseline, reduced to 1.1
Medication Use
  70% reduction in medication use at 90 days
  (Decongestants, antihistamines, steroids, anticholinergics)
Conclusions Laser ablation of PNN is a well-tolerated, safe, office or ambulatory procedure. Laser ablation of PNN improves both nasal congestion and rhinorrhea, also reduces medication use. Both allergic and non-allergic rhinitis appears to benefit from Laser Ablation of PNN. The results are similar to other treatment modalities. An ongoing analysis of long term outcomes in much larger series in a multicenter environment are next steps for study.

The Study: Endoscopic, Non-Contact Diode Laser Ablation of the Posterior Nasal Nerve Region in Treating Rhinitis.

Background: Posterior nasal nerve (PNN) surgery, or cryoablation, has been described as an alternative treatment for allergic and vasomotor rhinitis. We hypothesize that endoscopic (diode) laser ablation (ELA) is effective and less invasive than previously described methods.

Methods: The prospective study was performed with approval from the IRB. Thirty-two patients with chronic rhinitis and nasal congestion resistant to medical management were recruited. Total Nasal Symptom Score (TNSS) measurements were used to assess symptom severity and treatment outcomes. ELA was performed in the clinic under topical/local anesthesia in 11 patients, while the remaining 21 were treated under anesthesia in the operating room. The 400 micron uninitiated diode laser fiber tip with a malleable protective shaft was specially designed for PNN ablation. The fiber was pre-shaped according to the intranasal anatomy and endoscopically advanced toward the posterior middle meatus. The ELA method using a 940 nm diode laser at CW 5 W to bilaterally ablate the PNN region. Patients were followed up with for the first at 90 days after treatment.

Results: ELA was successfully completed in 97% of patients. No crusting, epistaxis, or other complications were observed. One patient could not be treated in the office due to limited endoscopic access. TNSS scores were reduced by 55% after 30 and by 51% after 90 days (p<0.001). Rhinitis and congestion scores were also decreased at 90 days by 44% and 48% respectively after treatment compared to the baseline (p<0.001).

Conclusion: ELA of the PNN region is safe and well tolerated both in the office and ambulatory settings. Symptom scores were significantly decreased after 30 and 90 days. This new minimally invasive method appears to be a promising alternative to other treatment methods.

Methods

The prospective study was performed with approval from the IRB. Thirty-two patients with chronic rhinitis and nasal congestion (including allergic and non-allergic rhinitis) who were resistant to medical management were recruited and treated. Patients were treated either in the office under topical/local anesthesia or in an ambulatory center when intranasal anatomy was not favorable and required general anesthesia. Particularly apprehensive, poorly cooperative patients with narrow nasal airway and limited endoscopic visualization to the posterior part of the nose. The Total Nasal Symptom Score (TNSS) was chosen to measure symptom severity and treatment outcomes. The TNSS is the sum of scores for the symptoms of nasal congestion, sneezing, nasal itching, and rhinorrhea at 30 and 90 days following the procedure, using a four point scale (0-3) where 0 indicates no symptoms, 1 indicates mild symptoms that are easily tolerated, 2 is awareness of bothersome but tolerable symptoms, and 3 is reserved for severe, hard to tolerate symptoms that interfere with daily activity. TNSS is calculated by adding the score for each of the symptoms to a total out of 12. Endoscopic laser ablation (ELA) was performed in the office for 11 patients, while the rest were treated under sedation in the operating room. The 940 nm diode laser (Epic-S, Biolase, Irvine, CA) with a 400 micron uninitiated malleable fiber tip, which was specially designed for ablation, was pre-shaped and endoscopically advanced toward the posterior middle meatus. The PNN region was ablated by using a continuous wave (CW) at 5 W in a noncontact mode for about 15-20 seconds. Mucosal blanching represented the end of treatment. ELA was performed bilaterally. Patients were followed up for 90 days to assess TNSS. Medication use was also recorded.

Results

All but one patient (96%) were able to complete the procedure. Ten patients were successfully treated in the office and twenty-one in the surgical center. Following procedure, pain was recorded on a 1-10 scale for office-treated patients and was found to be 1.8. No laser safety events were recorded. No crusting, headaches, facial pain, eye dryness, palatal numbness, or ear blockage were recorded at any follow-up visits.

Symptom scores after 30 days showed 55% overall improvement in TNSS. Mean score 7.1 (out of 12) at baseline, was reduced to 3.2. Symptom specific scores showed 48% improvement in rhinorrhea with 53% improvement in nasal congestion after 30 days. Symptom scores 90 days post procedure showed 51% overall improvement in TNSS with symptom-specific scores of 44% improvement in rhinorrhea and 48% improvement in congestion. Total medication use showed 70% reduction in medication use after 90 days. The results were similar in non-allergic 15 (47%) and allergic 17 (53%) patients.

Discussion

In the past, vidian nerve section paved the way to surgical therapy for rhinitis. Ablation of PNN is advantageous for neurectomy considering its feasibility and low complication rate. The recent gain in popularity of cryoablation led to newer studies using alternative technologies to treat the location of the posterior nasal nerves. Studies showed variation in the number and location of the nerves exiting the sphenopalatine (SP) foramen, with up to 20% branching. Furthermore, some authors believe that several small foramina exist alongside the nerves exiting the SP foramen, creating an anastomotic network. The branches of PNN can be found inferior and posterior to the sphenopalatine artery where the middle turbinate attaches to the lateral wall, and by locating the sphenopalatine artery at the sphenopalatine foramen, followed by transaction of a thin periosteum covering from the artery, which allows for clear vision of the nerve and artery.

To date, the only method of PNN surgery in use was direct identification under endoscopic guidance with appropriate nerve section. This method can be considered the gold standard. Histological changes are observed with long-lasting results of up to 48 months in a rat model. Endoscopic PNN section, however, is performed under general anesthesia, is time consuming, and requires meticulous dissection.

Cryotherapy, an ablation method of the PNN region, was developed as early as 1975 and performed with Frigitronics probes (Cooper Surgical, Trumbull, CT). The probe reaches $-70$ C to $-90$ C and has an effective thermal treatment radius of up to 3-4 mm as the temperature drops to OC at a 5 mm radius, with tissue necrosis appearing at the given radius. Common complications included epistaxis, nasal obstruction, nasal crusting, and ear blockage, none of which were reported to be serious. Postoperative bleeding, the most prevalent complication, was readily managed post op with topical therapies in most cases. Efficacy showed overall improvement in symptoms for over 60% of patients, with over 63% improvement in obstructive symptoms and over 77% of patients reporting decreased rhinorrhea. All but one recent study did not quantify the improvement. The only report studying TNSS showed improvement, with TNSS reducing significantly after 30 days (mean±standard deviation: $6.2\pm0.5$ at baseline, $2.6\pm0.3$ at 30 days, n=27, p<0.001) and a continued reduction observed after 90 ($2.7\pm0.4$, n=24, p<0.001). The new disposable device is a single-use Clari-Fix device (Stryker, previously Arrinex, Redwood City, CA), which is inserted into the nose and advanced endoscopically to the target area, then inflated. Likely due to the fact that the inflation was in proximity to the Eustachian tube, most patients felt ear fullness for a week, with an improvement in 74% of patients. The device's disadvantages are its cost and single-location application. Another common side effect is the brain-freeze-type headaches and some mucosal sloughing following the beginning of cryotherapy.

Diode laser PNN ablation as described in this study is a novel method for the management of chronic rhinitis that has failed medical management. As a method in progress, laser PNN ablation showed comparable results to ClariFix and fewer possible complications. The laser has been shown efficacious in the allergic and non-allergic rhinitis groups. Laser ablation enjoys the precision of a malleable fiber tip that can be pre-curved, controlled endoscopically, clearly mapping the PNN target area. In an office setting, the laser fiber can be more economical as a single-use device. In addition, the laser fiber tip can be used for various intranasal procedures, such as turbinate reduction or ablation of swell bodies.

Limitations of the current study include a relatively limited follow-up time. However, predicting from cryotherapy studies, changes beyond three months are limited, and we expect the results to continue to be effective at a later time. These encouraging results merit a larger multicenter study.

Conclusion

Laser ablation of the PNN is safe and well tolerated both in office and in ambulatory settings. Symptom scores were significantly decreased after both 30 and 90 days. This new minimally invasive endoscopic method is a promising alternative to other treatment modalities.

Figure 16:
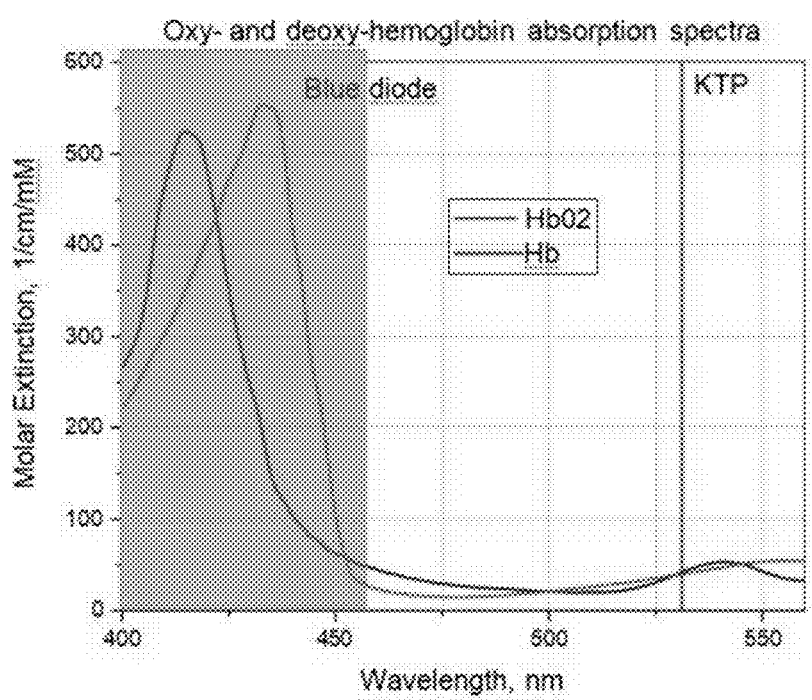
FIG. 16 is a chart of absorption spectra of oxy hemoglobin and deoxyhemoglobin with emission lines.

Another embodiment of the present invention is described now with reference to FIGS. 16 through 20B. In FIG. 16, there is shown a graph of hemoglobin and oxyhemoglobin absorption spectra and also showing emission lines of both KTP lasers and blue diode lasers. Blue light is absorbed by blood, but not by water, and is well suited for treating blood-rich soft tissues such as mucosa. The thermal tissue effect can be tuned in the range from that of potassium titanyl phosphate laser (KTP laser) to approximately five times stronger. A blue laser can cut and coagulate tissue at a distance of greater than 2 mm (like KTP laser) and be used in non-contact mode, which is not possible with electro/mechanical instruments. The blue diode laser also has the advantages of substantially lower cost compared to $CO_2$ laser at the same or approximately the same efficiency level.

Figure 17:
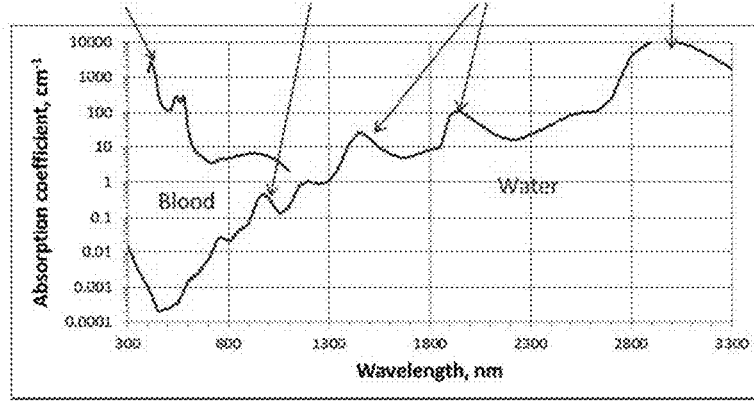
FIG. 17 is a chart of absorption against wavelength for various diode lasers.

With reference now to FIG. 17, there is shown a chart of the low water absorption and high Hgb (blood) absorption typical for blue laser. The blue laser is made by GaN diodes and cover a wavelength range of approximately 380-450 nanometers. Blue lasers have a general range wavelength of 360-480 nanometers and are within the scope of the invention. With FIG. 17, there is illustrated how the wavelength of 380-450 nanometers is best one to use over red colored mucosa and blood vessels of a patient, given the low water absorption and high blood absorption.

Figure 18:
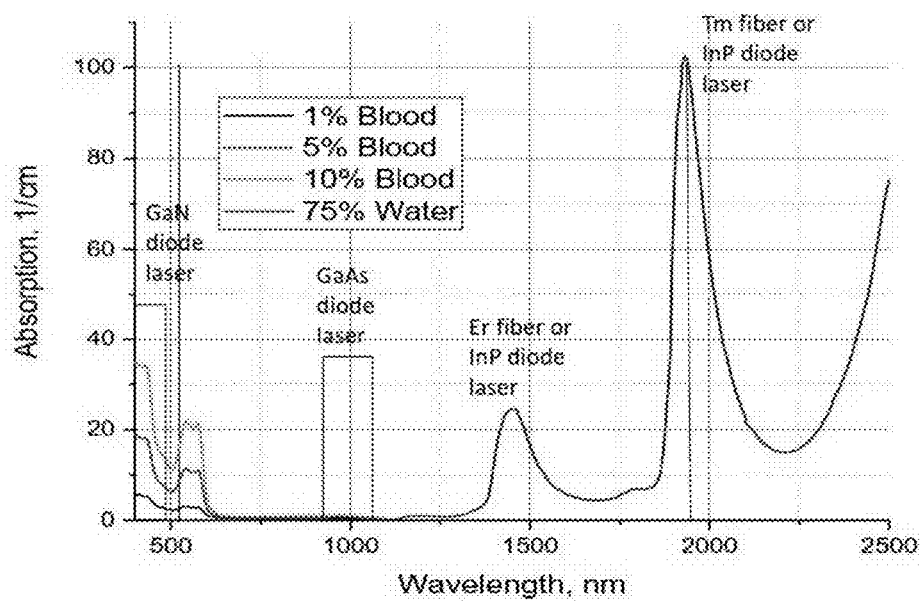
FIG. 18 is a graph of absorption of lasers with silica fiber in soft tissue.

FIG. 18 illustrates a chart of how blue lasers are absorbed with silica fiber in soft tissue. The GaN diode laser absorption is on the left side of the chart with absorption shown for 1% blood, 5% blood, 10% blood, and 75% water. The lasers at 400-500 nm made by GaN diodes are delivered by silica fiber transmitted through soft tissue and blood absorption. There is zero/minimal absorption by water.

The current clinical prototype is as follows: a wavelength of 445 nm is used, with an average power of up to 17 Watts and with a peak power of up to 30 Watts. The GaN blue diode laser (405-450 nm) with coefficient of absorption 10-150 cm-1 can be used for non-contact/focused beam cutting and vaporization similar to $CO_2$ laser in super pulse mode: 10-20 W peak power and 1-10 W average power.

Referring to FIGS. 19A and 19B, there is shown the solution provided with the embodiment of the present invention. The present invention uses an optical filter (for 445 nanometers) of transparent material, glass, polymer etc., that is positioned between the camera and the endoscope in connection with the delivery device described previously. The housing rim 300 with optical filter 303 between is placed between the camera and the endoscope at this position to prevent interference with the image and to allow the surgeon to clearly see the target area. This present invention is suitable for use with methods and delivery devices described earlier herein. In FIG. 19A, there is shown the rim/housing 300 which supports the optical filter 303, next to a measuring ruler 302 to provide the approximate dimensions, less than one inch (or less than 2.5 cm) outer diameter and less than one centimeter for the inner diameter opening which holds optical filter 303. In an embodiment, the dimension of the ring housing (the 7 mm filter) should be approximately 3 cm to fit the camera and endoscope assembly showing in FIG. 19B. In FIG. 19B, the rim 300 supporting optical filter 303 is placed over opening 305 within endoscopic camera housing 306 and camera locking system collar 308. The camera locking system 308 keeps the endoscope locked to the camera head. Once the rim 100 with filter 303 is in place so that filter 303 aligns over opening 305, the endoscopic camera housing 306 and camera locking system collar 308 are assembled with the endoscope head piece 304 placed over the assembly. The delivery device described above is connected to the endoscope and camera assembly so the blue laser light is delivered during the medical procedure.

A non-limiting table of specifications of optical filters which may be included for use in the present invention is presented below. Information is provided for the filters as both a light source and as a detector.

| Spectral | Light Source | Detector |
|---|---|---|
| Cut On | 460 nm | 460 nm |
| Peak Transmission- Min. acceptable % | >85% | >85% |
| Attenuation Range- short to long wavelengths | UV-450 nm | UV-450 nm |
| Attenuation OD- short to long wavelengths | OD5 average | $OD5_{10}$ average |
| Physical | | |
| Size/Diameter (mm) | 7.5 + 0/−.25mm | 9.5 + 0/−.25mm |
| Thickness: (Max) (mm) | 1.1 +/− 0.1 | 1.1 +/− 0.1 |
| Ring Mounted | unfinished | unfinished |

With the PNN ablation process performed with a blue laser or a 940 nm laser (such as the commercially available EPIC-S 940 nm laser) in the present invention, the medical professional/surgeon can see the blood vessels with the endoscope and since the tiny PNN nerves are running along the blood vessel(s), the surgeon is able to selectively ablate the vicinity of the blood vessels with the blue or the 940 nm laser in non-contact coagulation mode. This selective precision ablation method prevents collateral mucosa damage, reduces patient's pain and shortens the recovery time, improves the clinical outcome, and is a unique aspect of the laser delivery device. This is not and cannot be done with other RF or cryo-based means, or other current methods commercially available.

With the blue laser, during the process of the invention, the heating of the mucosal surface ideally should be approximately 60-70 Celsius to achieve reversible coagulation effect. Further, the blue laser has temperature feedback control parameters, which is a particular feature to the blue laser. As a result, the laser temporarily shuts off or creates pulsing action (on-oft) to maintain the tissue temperature constant until the end of the procedure. The blue laser has superior temperature control on tissue, selectivity to red colored mucosa surface and is highly absorbed by blood (Hgb), thus providing an additional wavelength range to the 940 nm laser device described above herein.

While illustrative embodiments of the invention have been described above, it is, of course, understood that many and various modifications will be apparent to those of ordinary skill in the relevant art, or may become apparent as the art develops. Such modifications are contemplated as being within the spirit and scope of the invention or inventions disclosed in this specification.

What is claimed is:

1. A process for treatment of rhinitis by laser ablation of posterior nasal nerve comprising:
    ablating the posterior nasal nerve by a laser delivery device with a fiber optic, said laser delivery device comprising a body with a proximal end and a distal end, said body including a handpiece section;
    said handpiece section having an opening at said proximal end;
    said handpiece section having an internal cavity extending from said opening and ending at a cavity base, said cavity configured to receive and connect with an optical module through said opening of said handpiece section;
    fiber optic having a proximal end fixed to said cavity base inside said body in a manner to receive laser energy beam from said optical module when said optical module is in use;
    said fiber optic extending from said cavity base through a distal end of said body; said fiber optic having a sheath covering said fiber optic and connected to said cavity base;
    a control knob on said body capable of moving from a first position to a second position, said control knob connected to a tube on said sheath internal to said body, said tube and said sheath with said fiber optic extending through said distal end of said body;
    a camera positioned on said tube external to said body, said camera and said tube moving from a first camera position to a second camera position when said control knob is moved from a first position to a second position;
    said fiber optic having said fiber tip extending from said sheath for delivering laser energy beam to a treatment area;
    said branches of posterior nasal nerve located above and below a middle turbinate; said fiber optic having said fiber tip inserted into an area of tissue near said middle turbinate;
    said laser delivery device providing a wavelength for therapeutic treatment that is delivered by said optical module through said laser delivery device;
    heating said tissue to approximately 60 to 70 degrees Celsius;
    positioning said fiber tip of said laser delivery device at a position above said middle turbinate;
    ablating lateral posterior superior branches of said posterior nasal nerve;
    positioning said fiber tip of said laser delivery device at a position below said middle turbinate;
    ablating lateral posterior inferior branches of said posterior nasal nerves.

2. The process according to claim 1 further comprising wherein said control knob of said laser delivery device rotates said camera.

3. The process according to claim 1 further comprising wherein said fiber optic having said sheath that is malleable.

4. The process according to claim 1 further comprising wherein the optic having said sheath that is adjustable and capable of configuration optimized for anatomical differences.

5. The process according to claim 1 further comprising where said laser delivery device delivers laser beam with a wavelength of approximately 940 nanometers when connected with said optical module.

6. The process according to claim 1, wherein said fiber optic of said laser delivery device is disposable.

7. The process according to claim 1 wherein said laser delivery device is re-usable.

8. The process according to claim 1 wherein said laser delivery device is reposable.

9. The process according to claim 1 wherein said laser delivery device is disposable.

* * * * *